(12) United States Patent
Mo et al.

(10) Patent No.: US 6,390,983 B1
(45) Date of Patent: May 21, 2002

(54) METHOD AND APPARATUS FOR AUTOMATIC MUTING OF DOPPLER NOISE INDUCED BY ULTRASOUND PROBE MOTION

(75) Inventors: Larry Y. L. Mo, Waukesha; Dean W. Brouwer, Muskego, both of WI (US)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 24 days.

(21) Appl. No.: 09/656,481

(22) Filed: Sep. 7, 2000

Related U.S. Application Data

(63) Continuation-in-part of application No. 09/349,586, filed on Jul. 9, 1999, now Pat. No. 6,296,612.

(51) Int. Cl.$^7$ .............................................. A61B 8/06
(52) U.S. Cl. ...................................................... 600/453
(58) Field of Search ........................... 600/437, 453–456

(56) References Cited

U.S. PATENT DOCUMENTS 5,827,969 A * 10/1998 Lee et al. .................... 600/455

* cited by examiner

*Primary Examiner*—Francis J. Jaworski
(74) *Attorney, Agent, or Firm*—Ostrager Chong & Flaherty LLP

(57) ABSTRACT

A method and an apparatus for monitoring the wall signal input to the wall filter of a spectral Doppler processor to check for probe-motion-induced clutter. This clutter is typically of higher frequency and amplitude than that due to normal vessel wall motion. Some additional threshold logic is used to check for energy within a frequency band greater than the normal wall signal frequencies. If significant energy above some "rattle" threshold is detected for a predefined time interval, the Doppler audio is automatically muted. This can be effected at one or more points within the normal Doppler audio signal path in a conventional scanner. If the rattling clutter is no longer detected, the Doppler audio is re-activated or ramped up smoothly.

25 Claims, 2 Drawing Sheets

METHOD AND APPARATUS FOR AUTOMATIC MUTING OF DOPPLER NOISE INDUCED BY ULTRASOUND PROBE MOTION

RELATED PATENT APPLICATION

This application is a continuation-in-part application claiming priority from U.S. patent application Ser. No. 09/349,586 filed on Jul. 9, 1999, U.S. Pat. No. 6,296,612.

FIELD OF THE INVENTION

This invention relates to ultrasonic diagnostic systems which measure the velocity of blood flow using spectral Doppler techniques. In particular, the invention relates to the continuous display of such information, including maximum and mean blood flow velocities.

BACKGROUND OF THE INVENTION

Ultrasonic scanners for detecting blood flow based on the Doppler effect are well known. Such systems operate by actuating an ultrasonic transducer array to transmit ultrasonic waves into the object and receiving ultrasonic echoes backscattered from the object. For blood flow measurements, returning ultrasonic waves are compared to a frequency reference to determine the frequency shifts imparted to the returning waves by moving objects including the vessel walls and the red blood cells inside the vessel. These frequency shifts translate into velocities of motion.

In state-of-the-art ultrasonic scanners, the pulsed or continuous wave Doppler waveform is computed and displayed in real-time as a gray-scale spectrogram of velocity versus time with the gray-scale intensity (or color) modulated by the spectral power. The data for each spectral line comprises a multiplicity of frequency data bins for different frequency intervals, the spectral power data in each bin for a respective spectral line being displayed in a respective pixel of a respective column of pixels on the display monitor. Each spectral line represents an instantaneous measurement of blood flow.

In the conventional spectral Doppler mode, an ultrasound transducer array is activated to transmit by a transmit ultrasound burst which is fired repeatedly at a pulse repetition frequency (PRF). The PRF is typically in the kilohertz range. The return radiofrequency (RF) signals are detected by the transducer elements and then formed into a receive beam by a beamformer. For a digital system, the summed RF signal from each firing is demodulated by a demodulator into its in-phase and quadrature (I/Q) components. The I/Q components are integrated (summed) over a specific time interval and then sampled. The summing interval and transmit burst length together define the length of the sample volume as specified by the user. This so-called "sum and dump" operation effectively yields the Doppler signal backscattered from the sample volume. The Doppler signal is passed through a wall filter, which is a high pass filter that rejects any clutter in the signal corresponding to stationary or very slow-moving tissue, including a portion of the vessel wall(s) that might be lying within the sample volume. The filtered output is then fed into a spectrum analyzer, which typically takes the complex Fast Fourier Transform (FFT) over a moving time window of 64 to 256 samples. The data samples within an FFT analysis time window will be referred to hereinafter as an FFT packet. The FFT output contains all the information needed to create the video spectral display as well as the audio output (typical diagnostic Doppler ultrasound frequencies are in the audible range).

For video display, the power spectrum is computed by taking the power, or absolute value squared, of the FFT output. The power spectrum is compressed and then displayed via a gray-scale mapping on the monitor as a single spectral line at a particular time point in the Doppler velocity (frequency) versus time spectrogram. The positive frequency [0:PRF/2] spectrum represents flow velocities towards the transducer, whereas the negative frequency [−PRF/2:0] spectrum represents flow away from the transducer. An automatic Doppler maximum/mean waveform tracing is usually performed after the FFT power spectrum has been compressed. The computed maximum/mean velocity traces are usually presented as overlay information on the spectrogram display.

For the audio Doppler output, the positive and negative frequency portions, or sidebands, of the FFT output are split into two separate channels representing the forward and reverse flow spectra respectively. For each channel, the sideband is reflected about the zero frequency axis to obtain a symmetric spectrum, which generates, after an inverse FFT (IFFT) operation, a real-valued flow signal in the time domain. Both the forward and reverse flow signals are converted into analog waveforms, which are fed to corresponding audio speakers.

During a spectral Doppler exam, the sonographer often needs to move the probe over an anatomical region surrounding some vascular system. Probe motion effects may also result simply from large tissue movements due to breathing or other body motion. Whenever the Doppler sample volume is being jerked around over body tissue, low-frequency clutter is generated which can be significantly stronger than vessel wall signals. Such probe-motion-induced clutter often exceeds the wall filter cutoff frequency, and will show up as blooming white (very strong) echoes right above the wall filter region in the spectral display. This can be considered as the audio counterpart of the "flash artifact" in color flow imaging. The annoying effect lies not so much in the video display, but in the Doppler audio: such clutter usually generates a loud rattle that may scare the patient and/or increase his/her anxiety level.

Some form of automatic gain control is usually available in conventional Doppler scanners. Automatic gain control is used to prevent large signals from saturating various points in the signal chain including the video display and/or audio speaker output. Automatic gain control generally consists of detecting the signal amplitude level and adjusting the gain down if the signal approaches a maximum allowable level. Such gain control does not specifically attempt to detect the presence of and to completely mute out the loud probe-motion-induced clutter noise.

There is a need for a Doppler processor that can monitor the I/Q data for the presence of probemotion-induced clutter before the I/Q data is wall filtered.

SUMMARY OF THE INVENTION

The present invention is a method and an apparatus for monitoring the wall signal input to the wall filter of a spectral Doppler processor to check for probe-motion-induced clutter. This clutter is typically of higher frequency and amplitude than that due to normal vessel wall motion. In accordance with the preferred embodiment of the invention, some additional threshold logic is used to check for energy within a frequency band greater than the normal wall signal frequencies. If significant energy above some "rattle" threshold is detected for a predefined time interval, the Doppler audio is automatically muted. This can be effected at one or more points within the normal Doppler audio signal path in a conventional scanner. If the rattling clutter is no longer detected, the Doppler audio is re-activated or ramped up smoothly.

In accordance with the preferred embodiment, a system noise model is used to predict the mean system noise power in a bandpass filter output. The mean system noise power predicted by the system noise model provides a noise threshold to gage how much probe-motion-induced clutter power is present in the current FFT packet. If no significant probe-motion-induced clutter is present, then the audio processing will not be turned off. If significant probe-motion-induced clutter power is present in the FFT packet, the audio processing is turned off.

It should be clear to those skilled in the art that the method of the invention can be implemented in hardware (e.g., a digital signal processing chip) and/or software.

DETAILED DESCRIPTION OF THE PREFERRED EMBODIMENTS

Figure 1:
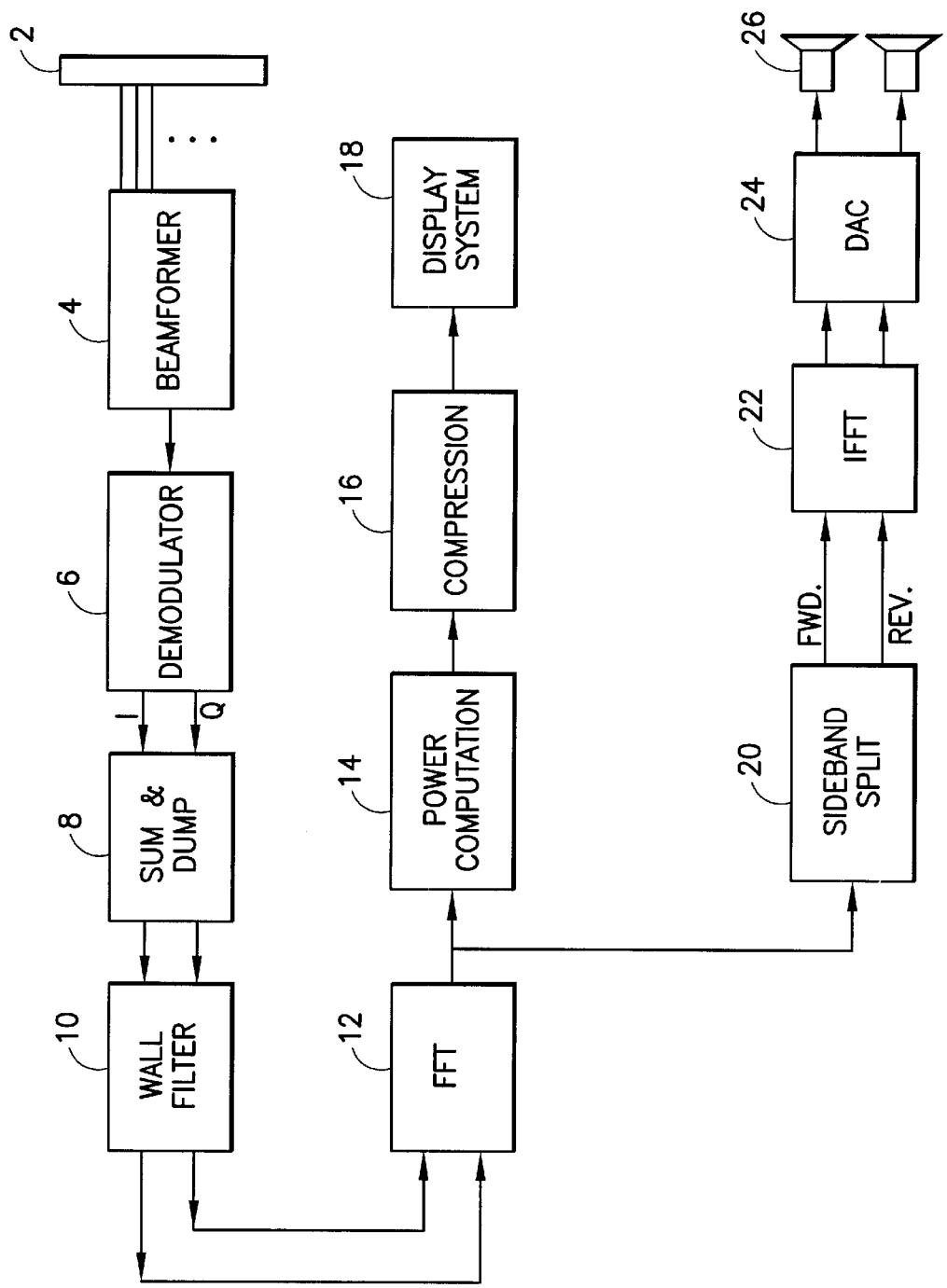
FIG. 1 is a block diagram of the basic signal processing chain in a conventional spectral Doppler imaging system.

A typical digital real-time ultrasonic imaging system having a spectral Doppler imaging mode is generally depicted in FIG. 1. An ultrasound transducer array 2 is activated to transmit by a transmit ultrasound burst which is fired repeatedly at a pulse repetition frequency (PRF). The PRF is typically in the kilohertz range. The return RF signals are detected by the transducer elements and then formed into a receive beam by a beamformer 4. For a digital system, the summed RF signal from each firing is demodulated by demodulator 6 into its in-phase and quadrature (I/Q) components. The I/Q components are integrated (summed) over a specific time interval and then sampled by a "sum and dump" block 8. The summing interval and transmit burst length together define the length of the sample volume as specified by the user. The "sum and dump" operation effectively yields the Doppler signal backscattered from the sample volume. The Doppler signal is passed through a wall filter 10 which rejects any clutter in the signal corresponding to stationary or very slow-moving tissue. The filtered output is then fed into a spectrum analyzer comprising a Fast Fourier Transform (FFT) block 12 and a power computation block 14. The FFT block 14 performs Fast Fourier transformation over a moving time window of 64 to 256 samples. Each FFT power spectrum output by block 14 is compressed (block 16) and sent to a known display system 18 comprising a timeline display memory, a video processor and a display monitor. The video processor maps the compressed FFT power spectral data to a grayscale for display on the monitor as a single spectral line at a particular time point in the Doppler velocity (frequency) versus time spectrogram.

For the audio Doppler output, the positive and negative frequency portions, or sidebands, of the output of the FFT block 12 are split by a sideband splitter 20 into two separate channels representing the forward and reverse (designated "FWD." and "REV." in FIG. 1) flow spectra respectively. For each channel, the sideband is reflected about the zero frequency axis to obtain a symmetric spectrum, which generates, after an inverse FFT (IFFT) operation (block 22), a real-valued flow signal in the time domain. Both the forward and reverse flow signals are converted into analog waveforms by respective digital-to-analog converters (DACs) 24. The analog waveforms are fed to corresponding audio speakers 26.

Figure 2:
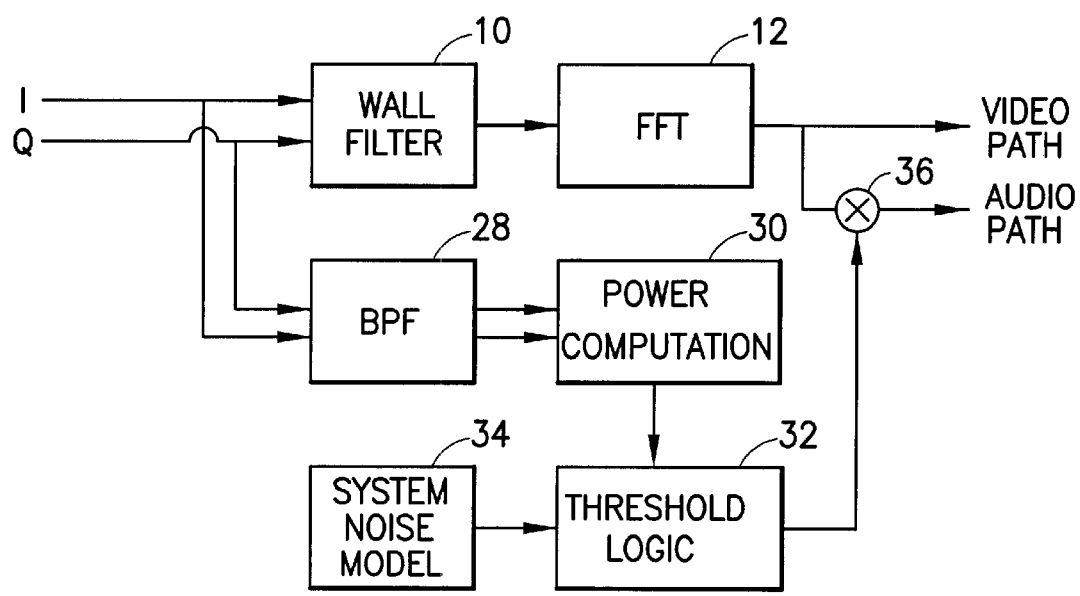
FIG. 2 is a block diagram showing an automatic audio muting mechanism in accordance with the preferred embodiment of the invention.

In accordance with the preferred embodiment of the invention, generally depicted in FIG. 2, an automatic audio muting mechanism receives the same signal which is input to the wall filter 10. In this particular embodiment, the audio muting mechanism is placed in parallel with the wall filter 10 and FFT block 12. The wall filter and FFT blocks are the same as those of a conventional scanner (shown in FIG. 1). The primary additional processing steps in accordance with the preferred method of practicing the invention are detailed below. It should be apparent that all the functional blocks shown in FIG. 2 can be implemented in software and/or hardware.

In accordance with the preferred embodiment, the I/Q data samples from the "sum and dump" block 8 are bandpass filter 28 is designed to pass a band of frequencies that are typical of probe motion, and to reject wall signals produced by slower-moving vessels and/or signals produced by very fast-moving blood flow. The instantaneous power of the filtered signal is then computed in block 30. The instantaneous power of the filtered signal is given by $I^2+Q^2$, which is a measure of the strength of the reflected signal. Preferably, the total power of the bandpass filter output, i.e., the sum of $(I_n^2+Q_n^2)$ over the FFT (or a fraction of the FFT) packet size M, is computed. A threshold logic block 32 checks if the signal power has exceeded a predefined "rattle" threshold. This threshold test may also be based on a moving average of the power over a predefined time interval, such as 20 msec. If the instantaneous or integrated power exceeds the threshold, the threshold logic block 32 will issue a flag to turn off the audio processing (i.e., mute the audio output). In the block diagram of FIG. 2, such a flag is equivalent to sending a "0" value from the threshold logic block 32 to a multiplier 36 situated in the audio path, i.e., situated in the line connecting the output of the FFT block 12 to the input to the sideband splitter 20 (see FIG. 1). If the audio is in a muted state, and the instantaneous or integrated power falls below the tolerance level, the threshold logic block 32 issues a "1" to the multiplier 36 to turn on the audio processing again, or it may issue a slow ramp-up function, e.g., a signal which increases linearly from "0" to "1", to gradually turn the audio back on.

As shown in FIG. 2, the threshold level may be derived from a system noise model 34 which can predict the system noise level given the current system setup and front-panel settings (e.g., the Doppler gain setting). This is a known art, especially for digital systems in which the main noise sources lie in the front-end analog electronics. The noise model may be implemented as a processor programmed to calculate a set of equations that predict the system noise, or in the form of a look-up table with pre-calculated values. The "rattle" threshold employed by the threshold logic block 32 is set at some predetermined level (i.e., threshold) above the noise level. That is, if the signal power exceeds this threshold, then it is considered to be noise caused by probe motion and the corresponding audio output will be quite annoying if it is not muted.

In accordance with the preferred embodiment, the system noise model 34 is used to predict the mean power of the system noise within the passband of the bandpass filter 28. In the most preferred embodiment, the model assumes an all-digital scanner whose system noise originates primarily from the pre-amplifier in each receive channel in the beamformer. The pre-amp Johnson noise is often specified as arms voltage per $Hz^{1/2}$ (e.g., 0 $nV/Hz^{1/2}$) at room temperature. Thus, knowing the equivalent noise bandwidths of all the filters in the Doppler signal path (from the demodulator to the "sum and dump" filter) should enable an absolute arms noise level to be computed as a function of system gain. Any quantization noise due to analog-to-digital conversion in the receiver can also be added in an appropriate manner. Further, knowing the sample volume position and aperture strategy in the spectral Doppler mode, it should be straightforward to compute the total system noise by summing over all active receive channels (including array apodization effects) for a given sample volume position. The mean noise power at the bandpass filter output can be computed based on the bandwidth of the bandpass filter 28. It should be apparent to those skilled in the art that similar noise models can be developed for scanners whose Doppler signal paths differ from the basic structure of FIG. 1. Also, while a system noise model is clearly most efficient from an implementation standpoint, a LUT with multiple inputs can be used to perform the same function. Such a LUT can be established either by noise calibration measurements or by simulating the system noise model. In the first alternative, the system is pre-calibrated by trying different combinations of gain settings, recording the resulting noise values and storing those gain settings and corresponding noise values in a LUT. In the second alternative, the noise model values are pre-computed and stored in a LUT.

While the invention has been described with reference to preferred embodiments, it will be understood by those skilled in the art that various changes may be made and equivalents may be substituted for elements thereof without departing from the scope of the invention. In addition, many modifications may be made to adapt a particular situation to the teachings of the invention without departing from the essential scope thereof. Therefore it is intended that the invention not be limited to the particular embodiment disclosed as the best mode contemplated for carrying out this invention, but that the invention will include all embodiments falling within the scope of the appended claims.

As used in the claims, the term "digital signal processor" includes digital signal processing hardware and/or software.

What is claimed is:

1. A system for producing audible sound waves from electrical signals representing sequences of samples of Doppler signals acquired from a sample volume containing moving ultrasound scatterers, comprising:
   an ultrasound probe;
   a data acquisition subsystem connected to said ultrasound probe for acquiring Doppler signal samples;
   a digital signal processor for processing said Doppler signal samples to produce frequency data representing the velocities over time of ultrasound scatterers in said sample volume and directional flow data representing the flow of ultrasound scatterers in a predetermined direction in said sample volume;
   an audio subsystem for generating audible sound waves which are a function of the frequency data produced by said digital signal processor; and
   an audio muting subsystem for de-activating said audio subsystem in the event that significant energy above a threshold is detected within a frequency band associated with probe-motion-induced clutter in said Doppler signal samples,
   wherein said audio muting subsystem comprises a bandpass filter designed to pass a band of frequencies that are characteristic of motion of said ultrasound probe.

2. The system as recited in claim 1, wherein said digital signal processor comprises a wall filter and a Fast Fourier transformer.

3. The system as recited in claim 1, wherein said bandpass filter is designed to reject signals produced by vessel walls.

4. The system as recited in claim 1, wherein said bandpass filter is designed to reject signals produced by very fast-moving blood flow.

5. The system as recited in claim 1, wherein said audio muting subsystem further comprises means for computing the instantaneous power of a signal output by said bandpass filter.

6. The system as recited in claim 5, wherein said audio muting subsystem further comprises threshold logic for detecting if the signal power output by said bandpass filter is in excess of said threshold.

7. The system as recited in claim 5, wherein said audio muting subsystem further comprises threshold logic for detecting if a moving average of the signal power output by said bandpass filter is in excess of said threshold for a predefined time interval.

8. The system as recited in claim 1, wherein said data acquisition subsystem comprises:
   a transmitter for transmitting a multiplicity of pulses of ultrasound into a sample volume of ultrasound scatterers in succession;
   a receiver for acquiring a respective sequence of successive samples of Doppler signals following each pulse; and
   a demodulator for demodulating said Doppler signal samples into in-phase and quadrature components, wherein said digital signal processor comprises:
      first and second wall filters for substantially rejecting clutter in the in-phase and quadrature components corresponding to stationary or very slow-moving tissue; and
      a spectrum analyzer for producing spectral data by Fast Fourier transformation of the wall-filtered in-phase and quadrature components, and wherein said audio system comprises:
         means for extracting frequency-domain directional flow data from said spectral data; and
         means for transforming said frequency-domain directional flow data into time-domain directional flow data.

9. The system as recited in claim 8, further comprising a display system for displaying said spectral data.

10. A system for producing audible sound waves from electrical signals representing sequences of samples of Doppler signals acquired from a sample volume containing moving ultrasound scatterers, comprising:
    an ultrasound probe;
    a data acquisition subsystem connected to said ultrasound probe for acquiring Doppler signal samples;
    a digital signal processor for processing said Doppler signal samples to produce frequency data representing the velocities over time of ultrasound scatterers in said sample volume and directional flow data representing the flow of ultrasound scatterers in a predetermined direction in said sample volume;
    an audio subsystem for generating audible sound waves which are a function of the frequency data produced by said digital signal processor; and
    an audio muting subsystem for de-activating said audio subsystem in the event that significant energy above a threshold is detected within a frequency band associated with probe-motion-induced clutter in said Doppler signal samples, wherein said threshold is derived from a system noise model based on settings of operational parameters.

11. A system for producing audible sound waves from electrical signals representing sequences of samples of Doppler signals acquired from a sample volume containing moving ultrasound scatterers, comprising:

an ultrasound probe;

a data acquisition subsystem connected to said ultrasound probe for acquiring Doppler signal samples;

a digital signal processor for processing said Doppler signal samples to produce frequency data representing the velocities over time of ultrasound scatterers in said sample volume and directional flow data representing the flow of ultrasound scatterers in a predetermined direction in said sample volume;

an audio subsystem for generating audible sound waves which are a function of the frequency data produced by said digital signal processor; and an audio muting subsystem for de-activating said audio subsystem in the event that significant energy above a threshold is detected within a frequency band associated with probe-motion-induced clutter in said Doppler signal samples, wherein said audio muting subsystem comprises a detector designed to detect clutter in said Doppler signal samples which is characteristic of motion of said probe and a switch having a first input coupled to receive said frequency data from said digital signal processor, a second input coupled to said detector, and an output coupled to said audio system, said switch comprising a multiplier and said detector outputting a null signal to said second input of said multiplier when said clutter is detected.

12. The system as recited in claim 11, wherein said detector outputs a ramp signal to said second input or said multiplier when clutter is no longer detected.

13. A method for selectively producing audible sound waves from electrical signals representing sequences of samples of Doppler signals acquired from a sample volume containing moving ultrasound scatterers, comprising the steps of:

processing Doppler signal samples to produce frequency data representing the velocities over time of ultrasound scatterers in said sample volume;

detecting whether significant energy above a threshold is present within a frequency band associated with probe-motion-induced clutter in said Doppler signal samples; and generating audible sound waves which are a function of said frequency data only if significant energy above said threshold is not detected, wherein said detecting step comprises the step of bandpass filtering to pass only a band of frequencies that are characteristic of motion of said ultrasound probe.

14. The method as recited in claim 13, wherein said bandpass filtering step comprises the step of rejecting signals produced by vessel walls.

15. The method as recited in claim 13, wherein said bandpass filtering step comprises the step of rejecting signals produced by very fast-moving blood flow.

16. The method as recited in claim 13, wherein said detecting step further comprises the step of computing the instantaneous power of said bandpass-filtered signal.

17. The method as recited in claim 16, wherein said detecting step further comprises the step of detecting if said power is in excess of said threshold.

18. The method as recited in claim 16, wherein said detecting step further comprises the step of detecting if a moving average of said power is in excess of said threshold for a predefined time interval.

19. A method for selectively producing audible sound waves from electrical signals representing sequences of samples of Doppler signals acquired from a sample volume containing moving ultrasound scatterers, comprising the steps of:

processing Doppler signal samples to produce frequency data representing the velocities over time of ultrasound scatterers in said sample volume;

detecting whether significant energy above a threshold is present within a frequency band associated with probe-motion-induced clutter in said Doppler signal samples; and generating audible sound waves which are a function of said frequency data only if significant energy above said threshold is not detected, wherein said threshold is derived from a system noise model based on settings of operational parameters.

20. A method for producing audible sounds representing flow of ultrasound scatterers, comprising the steps of:

transmitting pulses of ultrasound into a sample volume containing moving ultrasound scatterers;

acquiring a multiplicity of successive samples of Doppler signals backscattered from said sample volume;

rejecting clutter in said Doppler signals corresponding to stationary or very slow-moving tissue;

processing said Doppler signals to produce frequency data representing the velocities over time of ultrasound scatterers in said sample volume;

detecting whether significant energy above a threshold is present within a frequency band associated with probe-motion-induced clutter in said Doppler signals; and generating audible sound waves which are a function of said frequency data only if significant energy above said threshold is not detected, wherein said detecting step comprises the step of bandpass filtering to pass only a band of frequencies that are characteristic of motion of said ultrasound probe.

21. The method as recited in claim 20, wherein said generating step comprises the steps of:

extracting frequency-domain directional flow data corresponding to flow in a predetermined direction from said frequency data;

transforming said frequency-domain directional flow data into time-domain directional flow data;

converting said time-domain directional flow data into analog audio signals; and feeding said analog audio signals into an audio speaker.

22. An ultrasound imaging system comprising an ultrasound probe, an audio speaker subsystem, and a computer programmed to perform the following steps:

controlling said probe to transmit pulses of ultrasound into a sample volume containing moving ultrasound scatterers;

controlling said probe to acquire a multiplicity of successive samples of Doppler signals backscattered from said sample volume;

rejecting clutter in said Doppler signals corresponding to stationary or very slow-moving tissue;

processing said Doppler signals to produce frequency data representing the velocities over time of ultrasound scatterers in said sample volume;

detecting whether significant energy above a threshold is present within a frequency band associated with probe-motion-induced clutter in said Doppler signals; and controlling said audio speaker subsystem to emit audible sound waves which are a function of said frequency data only if significant energy above said threshold is not detected, wherein said detecting step comprises the step of bandpass filtering to pass only a band of frequencies that are characteristic of motion of said ultrasound probe.

23. The system as recited in claim 22, wherein said detecting step further comprises the step of computing the instantaneous power of said bandpass-filtered signal.

24. The system as recited in claim 23, wherein said detecting step further comprises the step of detecting if said power is in excess of said threshold.

25. The system as recited in claim 23, wherein said detecting step further comprises the step of detecting if a moving average of said power is in excess of said threshold for a predefined time interval.

* * * * *

UNITED STATES PATENT AND TRADEMARK OFFICE
CERTIFICATE OF CORRECTION

PATENT NO.   : 6,390,983 B1
DATED        : May 21, 2002
INVENTOR(S)  : Larry Y.L. Mo et al.

It is certified that error appears in the above-identified patent and that said Letters Patent is hereby corrected as shown below:

Column 4,
Line 18, insert -- passed through a linear bandpass filter (BPF) 28.
The -- after "are".

Column 5,
Line 1, "arms" should read -- a rms --.

Signed and Sealed this

Twenty-eighth Day of January, 2003

JAMES E. ROGAN
*Director of the United States Patent and Trademark Office*